US009991661B2

United States Patent
Ramachandran

(10) Patent No.: US 9,991,661 B2
(45) Date of Patent: Jun. 5, 2018

(54) CLEANING SYSTEM FOR SLIP RING OF MEDICAL IMAGING APPARATUS

(71) Applicant: General Electric Company, Schenectady, NY (US)

(72) Inventor: Gowrishankar Ramachandran, Bangalore (IN)

(73) Assignee: General Electric Company, Schenectady, NY (US)

(*) Notice: Subject to any disclaimer, the term of this patent is extended or adjusted under 35 U.S.C. 154(b) by 71 days.

(21) Appl. No.: 15/281,289

(22) Filed: Sep. 30, 2016

(65) Prior Publication Data
US 2017/0093109 A1    Mar. 30, 2017

(30) Foreign Application Priority Data
Sep. 30, 2015 (IN) .......................... 5224/CHE/2015

(51) Int. Cl.
| H01R 43/14 | (2006.01) |
| A61B 6/00 | (2006.01) |
| A61B 6/03 | (2006.01) |
| B08B 5/04 | (2006.01) |
| B08B 1/00 | (2006.01) |

(52) U.S. Cl.
CPC ............. *H01R 43/14* (2013.01); *A61B 6/035* (2013.01); *A61B 6/467* (2013.01); *A61B 6/56* (2013.01); *A61B 6/586* (2013.01)

(58) Field of Classification Search
CPC ........... A61B 6/035; A61B 6/467; A61B 6/56; A61B 6/586; H01R 43/14
See application file for complete search history.

(56) References Cited

U.S. PATENT DOCUMENTS

| 2,898,487 A * | 8/1959 | Uhink ................... H01R 43/14 310/228 |
| 5,402,461 A * | 3/1995 | Kudo ...................... A61B 6/56 378/111 |
| 2005/0259782 A1* | 11/2005 | Kasuya .................. A61B 6/032 378/15 |
| 2006/0067615 A1* | 3/2006 | Schilling ................. A61B 6/56 385/25 |
| 2015/0129319 A1* | 5/2015 | D'Silva ................ H01R 39/385 175/320 |

FOREIGN PATENT DOCUMENTS

| CN | 202050153 U | * 11/2011 | |
| GB | 831506 A | * 3/1960 | ............ H01R 43/14 |
| JP | 05076525 A | * 3/1993 | |
| JP | 2011115325 A | * 6/2011 | |
| WO | WO 0078216 A1 | * 12/2000 | .............. A61B 6/56 |

\* cited by examiner

*Primary Examiner* — Marc Carlson

(57) ABSTRACT

A cleaning system for cleaning a slip ring arranged to be rotatable about an axis is disclosed. The cleaning system includes a cleaner assembly configured so as to be positionable to contact the slip ring. The cleaner assembly is capable of moving along the slip ring for cleaning. A control unit is configured to control the functioning of the cleaner assembly based on user input.

20 Claims, 4 Drawing Sheets

CLEANING SYSTEM FOR SLIP RING OF MEDICAL IMAGING APPARATUS

FIELD OF THE INVENTION

The subject matter disclosed herein relates to cleaning of slip rings. More specifically it relates to automatic cleaning of a slip ring that is stationary in a medical imaging apparatus.

BACKGROUND OF THE INVENTION

Computed tomography (CT) imaging systems have become ubiquitous in the fields of medical diagnostics and treatment. CT systems typically include an X-ray source, such as a conventional X-ray tube, positioned in a diametrically opposed location from a detector. The source and detector rotate on a gantry, and the source produces beams of X-ray radiation that are directed through a subject of interest and impact the detector on the opposite side of the gantry. The emitted radiation is attenuated by features and structures of the subject, and the transmitted radiation is measured by the detector. Such CT systems use acquired data to reconstruct images of internal features of a variety of subjects, including human and animal patients in a medical diagnostic context, internal configurations and components of parts and parcels, and so forth.

Conventional CT systems rotate at increasingly high speeds to improve the resolution of the resulting reconstructed images. Such high speeds have increased the quantity of image data that is acquired during the CT scan. However, these high speed CT systems utilize slip rings to transfer data from the rotating gantry to permanent disk drives (or other memory circuits) located in a stationary computer. A slip ring includes multiple data lines for transferring the data from the detector and power lines to transfer the power. One or more brush blocks i.e. metal blocks may be in contact with the data lines and power lines of the slip ring while it rotates to transfer the detector data and transfer power to gantry and other CT parts. The brush block, which contains the Carbon brushes, remains stationary and the slip ring continues to rotate or vice versa and due to this constant contact there may be normal wear and tear that results in carbon dust accumulation on the slip ring. The slip ring needs to be periodically cleaned to remove the carbon dust. The service engineer opens the CT machine to access the slip ring and then manually cleans the slip ring which is a tedious task. During the cleaning process the slip ring will be stationary. The cleaning process also takes time and accessing the slip ring also may be difficult. Thus there is a need for an improved system for cleaning the slip ring.

SUMMARY OF THE INVENTION

An object of embodiments of the invention is to provide an improved system for cleaning a slip ring, which overcomes one or more drawbacks of the prior art. This is achieved by the system having the capability of as defined in the independent claim.

One advantage with the disclosed cleaning system is that it can automatically clean a slip ring at periodic time intervals without opening a cover of the medical imaging apparatus for manually cleaning the slip ring. Further the cleaning system can be actuated or activated based on user's command or control. The cleaning system can be set to operate at predefined time intervals so that it can automatically start cleaning the slip ring. The cleaning system is also capable of predicting and notifying the life of the cleaning system to the user so that it can be serviced and brushes of the cleaning system can be replaced conveniently before breakdown.

In an embodiment a cleaning system for cleaning a slip ring arranged to be rotatable about an axis is disclosed. The cleaning system includes a cleaner assembly configured so as to be positionable to contact the slip ring. The cleaner assembly is capable of moving along the slip ring for cleaning. A control unit is configured to control the functioning of the cleaner assembly based on user input.

In another embodiment, a medical imaging apparatus having a slip ring arranged to be rotatable about an axis is disclosed. The medical imaging apparatus comprises a cleaner assembly configured so as to be positionable to contact the slip ring, wherein the cleaner assembly is capable of moving along the slip ring for cleaning; and a control unit is configured to control the functioning of the cleaner assembly based on user input.

A more complete understanding of the present invention, as well as further features and advantages thereof, will be obtained by reference to the following detailed description and drawings.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical and other changes may be made without departing from the scope of the embodiments. The following detailed description is, therefore, not to be taken as limiting the scope of the invention.

As discussed in detail below, embodiments of a cleaning system for cleaning a slip ring arranged to be rotatable about an axis is disclosed. The cleaning system includes a cleaner assembly configured so as to be positionable to contact the slip ring. The cleaner assembly is capable of moving along the slip ring for cleaning. A control unit is configured to control the functioning of the cleaner assembly based on user input. The cleaning system is used for cleaning the slip ring of a medical imaging apparatus.

Typically, in a medical imaging apparatus such as a computed tomography (CT) imaging system, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Figure 1:
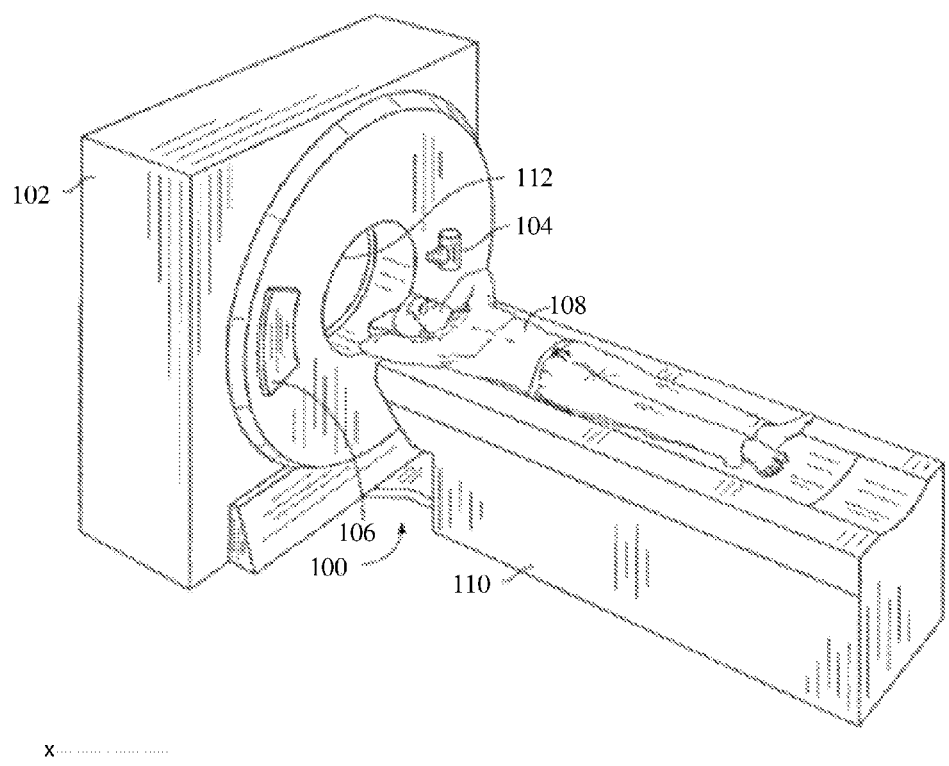
FIG. 1 is a schematic illustration of a computed tomography (CT) imaging system according to an embodiment.

Referring now specifically to FIG. 1, a computed tomography (CT) imaging system 100 is shown as including a gantry 102. The gantry 102 has a radiation source such as x-ray source 104 that projects a beam of x-rays toward a detector array 106 on the opposite side of the gantry 102. The detector array 106 is formed by a plurality of detector modules that together sense the projected x-rays that pass through an object 108 such as, but not limited to, a medical patient 108. Each detector module produces an electrical signal that represents the intensity of an impinging x-ray beam and hence the attenuation of the beam as it passes through patient 108.

During a scan to acquire x-ray projection data, the gantry 102 and the components mounted thereon rotate about a center of rotation. A motorized table 110 positions the patient 108 relative to the gantry 102. Particularly, the table 110 moves portions of patient 108 through a gantry opening 112 during a scan.

Figure 2:
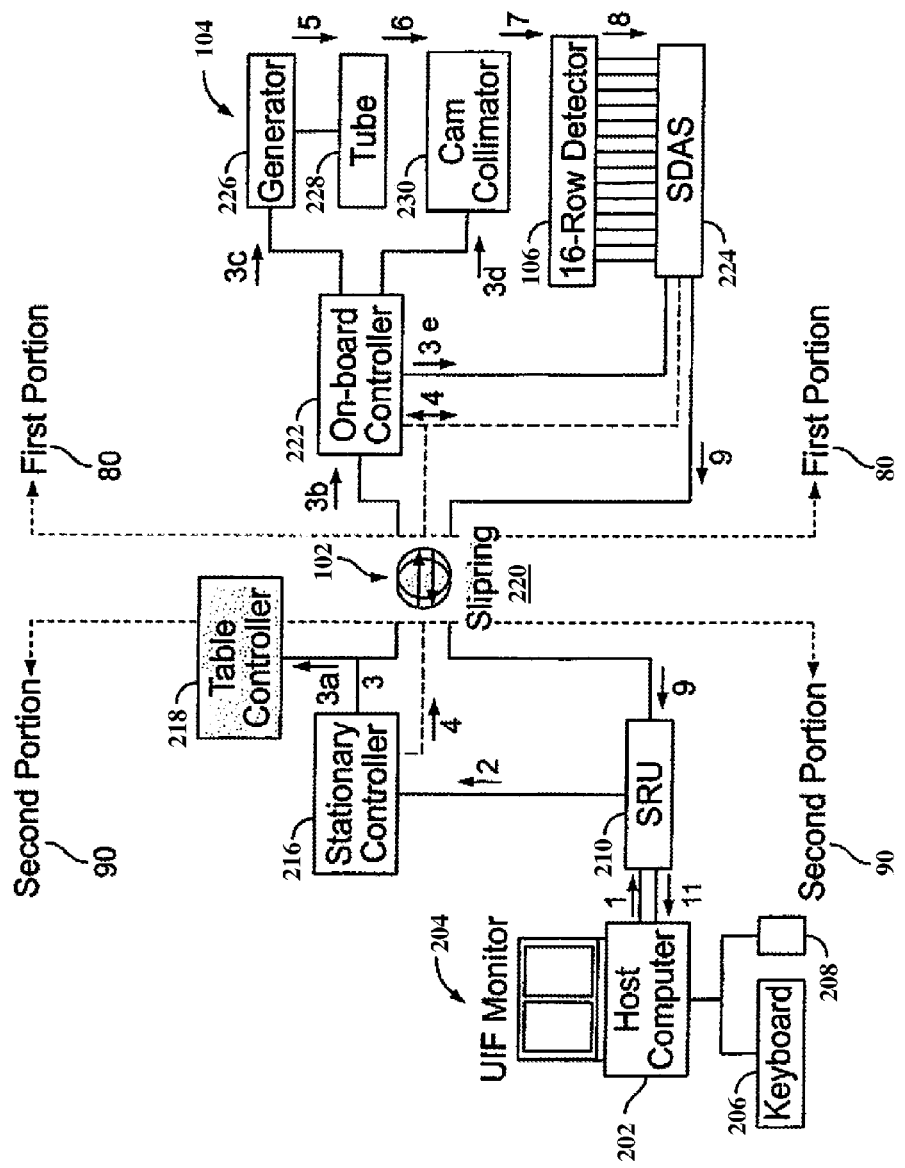
FIG. 2 illustrates is a block schematic diagram of the system illustrated in FIG. 1.

FIG. 2 is a block schematic diagram of the system illustrated in FIG. 1. As shown in FIG. 2, system 100 includes a host computer 202 coupled to a monitor (user interface) 204 for displaying images and messages to an operator. The computer 202 also is coupled to a keyboard 206 and an input device 208 such as a mouse 208 to enable the operator to input information and commands to computer 202. The computer 202 is coupled to a scan and reconstruction control unit (SRU) 210. The SRU 210 also includes image generation controls. In one embodiment, the SRU 210 includes a SGI PCI-based central processing unit that operates on an IRIX operating system. The SRU 210 also includes an interface processor for interfacing with the data acquisition system (described below), and a scan data correction digital signal processing board for performing preprocessing, which is known in the art. The SRU 210 further includes an image generator for filtered back projection and post-processing operations, as is known in the art.

A stationary controller 216 is connected to SRU 210, and the stationary controller 216 is coupled to a table controller 218. The stationary controller 216 also is connected, through a slip ring 220, to an on-board controller 222 and a scalable data acquisition system (SDAS) 224 or a global data acquisition system (GDAS), which is used in some embodiments. The slip ring 220 enables contactless transmission of signals across the slip ring boundary and supports the necessary bandwidth for transmission of data and commands across the boundary. A brush unit (for e.g. a carbon brush) comes in the contact with the slip ring 220 and rotates along the slip ring 220 to collect data from the slip ring 220 and provide power. The slip ring 220 typically includes data lines and power lines that can carry data and power respectively. Due to constant contact and movement along the slip ring 220 by the brush unit, dust may be deposited on the slip ring 220. The dust deposition may affect the performance of slip ring 220 affecting data reading from the slip ring 220 and power transmission to the slip ring 220. The SDAS 224 or GDAS samples and acquires the data from the detector array 106 and converts the sampled analog signals to digital signals. The on-board controller 222 controls operation of the x-ray source 104 and operation of the DAS 224. The x-ray source 104 includes a high voltage generator 226 coupled to an x-ray tube 228. The beams projected by the x-ray tube 228 pass through a pre-patient cam collimator 230 and impinge upon detector 106 (illustrated as a 16 row detectors). The cam collimator 230 also is controlled by the on-board controller 222. Outputs from the detector 106 are supplied to DAS 224.

Figure 3:
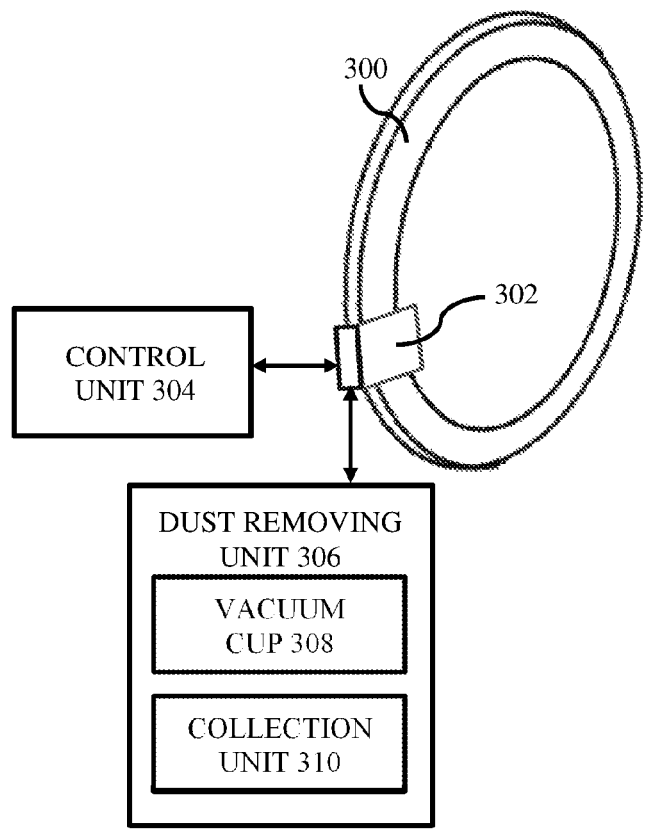
FIG. 3 illustrates a slip-ring having a cleaner assembly for cleaning according to an embodiment.

FIG. 3 illustrates a slip-ring 300 having a cleaner assembly 302 for cleaning according to an embodiment. The cleaner assembly 302 is moved to contact the slip ring 300 and then moved along the slip-ring 300 to remove the dust. The operation of the cleaner assembly 302 is controlled by a control unit 304. The operation includes, engaging (i.e. coming in contact) with the slip-ring 300 and disengaging the cleaner assembly 302, and cleaning the slip-ring 300 by moving the cleaner assembly 302 along it. In an embodiment, the control unit 304 receives user's input for performing the operations. The control unit 304 may be connected to a control user interface of the medical imaging apparatus. The user (i.e. an operator or clinician or medical expert) can provide inputs through the user interface. For instance, the user can engage the cleaner assembly 302 with the slip-ring 300 by providing user inputs through the control user interface acting as a control panel. The control panel may be configured as a touch based user interface in a medical imaging apparatus. The medical imaging apparatus may be, but not limited to, a computed tomography (CT) imaging device, an X-ray device and so on. In another embodiment, the control panel may be present in a console room that is separate from a room having the medical imaging apparatus. In an embodiment, the user input from the user may be to clean the slip-ring 300. The control unit 304 receives this input and sends command signal(s) to position the cleaner assembly 302 to contact the slip-ring 300 and then move along it to perform cleaning operation. The control unit 304 sends another command signal to disengage the cleaner assembly 302 from the slip-ring 300 in response to user's input received at the control user interface. The cleaner assembly 302 stops cleaning the slip-ring 300 and disengages. Once the slip-ring 300 is cleaned, it can be used to perform transmission of data and power. Further, the cleaner assembly 302 can simplify the process of cleaning the slip-ring 300 by avoiding manual cleaning.

In another embodiment, the cleaner assembly 302 can be pre-programmed to perform the operations on the slip-ring 300. The pre-programming can be performed based on user inputs received at the control user interface. In this embodiment, the control unit 304 can control the cleaner assembly 302 to perform the cleaning of the slip-ring 300 at predefined intervals. Here, the cleaner assembly 302 engages with the slip-ring 300 to perform cleaning for a predefined time interval and then disengages automatically. The slip-ring 300 is again cleaned by the cleaner assembly 302 after a predefined time period. This may be a cyclic process and programmed by the user through the control user interface. As the cleaning process is automatically controlled there is no user intervention.

Figure 4:
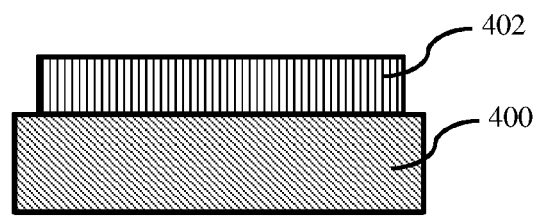
FIG. 4 illustrates a cleaner assembly including a supporting unit and an eraser according to another embodiment.

In an embodiment, the cleaner assembly 302 includes a supporting unit 400 and an eraser 402 as illustrated in FIG. 4. An exemplary embodiment may have the eraser 402 including a plurality of brush bristles that removes the dust once the cleaner assembly 302 moves along the slip-ring 300. More specifically, the brush bristles come in contact with surface of the slip-ring 300 to remove and collect the dust. As shown in FIG. 4, the eraser 402 is fixed on the supporting unit 400. The supporting unit 400 may be a solid block that supports the eraser 402. However, it may be envisioned that the cleaner assembly 302 can have any other structural and/or functional configuration known in the art without deviating from scope of this disclosure. The dust collected in the cleaner assembly 302 needs to be removed so that the cleaner assembly 302 can be used without any failure.

The cleaner assembly 302 needs to be cleaned once in a while to remove the dust using a dust removing unit 306 as illustrated in FIG. 3, according to an exemplary embodiment. The dust removing unit 306 is also controlled by the control unit 304. The control unit 304 receives user input for operating the dust removing unit 306. The dust removing unit 306 may include a vacuum cup 308 and a collection unit 310. The vacuum cup 308 can be positioned with respect to the eraser 402 to collect the dust. The vacuum cup 308 may cover the eraser 402 and form an air-tight enclosure around the eraser 402. The vacuum cup 308 may function based on a vacuum based technique to draw the dust from the eraser 402. The positioning of the vacuum cup 308 and its operation may be controlled by the control unit 304. In embodiment, the vacuum cup 308 may be a single vacuum cup. In another embodiment, the vacuum cup 308 may include multiple cups that can function based on vacuum based technique to collect the dust.

The dust collected by the vacuum cup 308 is then deposited into a collection unit 310. The collection unit 310 may be a compartment that may be connected to the vacuum cup 308. The dust from the vacuum cup 308 may be deposited into the collection unit 310. In another embodiment, there may be another vacuum unit that may be capable of drawing the dust from the vacuum cup 308 and depositing it in the collection unit 310. Here, the vacuum unit may be operated by the control unit 304. In an alternate embodiment, the vacuum cup 308 may be tilted or shaken to allow the dust to be dropped into the collection unit 310 after vacuum function is disabled. However, there may be other techniques or constructional and/or functional structures known in the art that may be utilized or formed to collect and store the dust in the collection unit 310 in different exemplary embodiments. In an embodiment, the collection unit 310 may be also operated by the control unit 304 for collecting the dust.

In an embodiment, the control unit 304 may operate the collection unit 310 in a pre-programmed manner based on user inputs. The user can preprogram the operation of the collection unit 310 through the control user interface. The control unit 304 can be preprogrammed to operate the collection unit 310 to collect the dust from the vacuum cup 308 at predefined time intervals.

Figure 5:
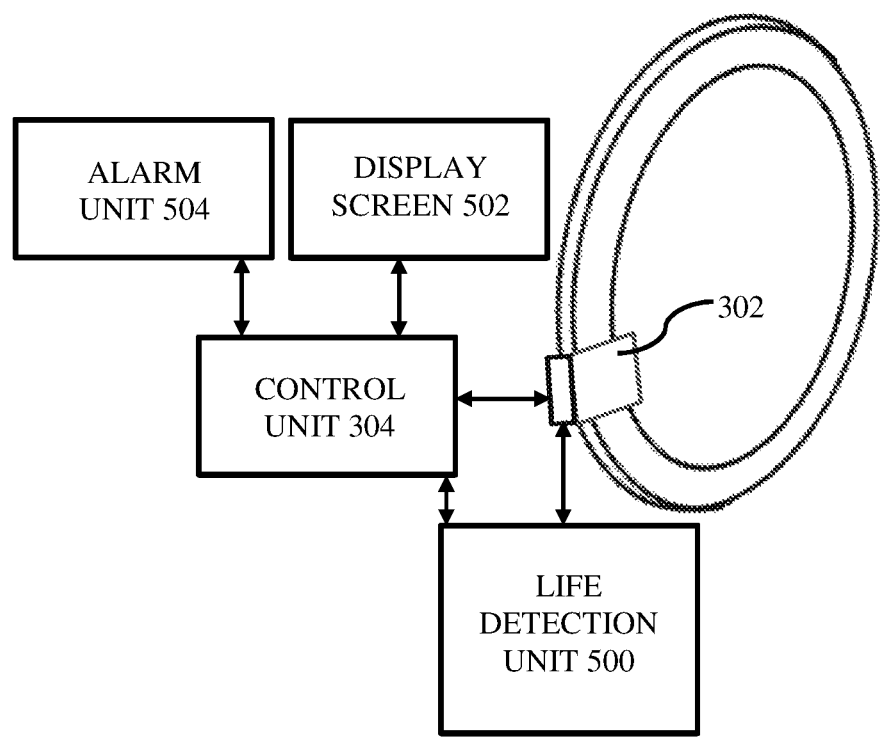
FIG. 5 illustrates a life detection unit capable of monitoring the life of the cleaner assembly according to an embodiment.

After multiple usages, the cleaner assembly 302 may wear out and need to be replaced. In an embodiment, the eraser 402 may wear out due to usage and the user needs to be aware to get them replaced. FIG. 5 illustrates a life detection unit 500 capable of monitoring the life of the cleaner assembly 302 according to an embodiment. In an embodiment, the life detection unit 500 may include multiple sensors that may be positioned in the cleaner assembly 302 to monitor the wear and tear occurring in the cleaner assembly 302. For example, the sensors may be capable of determining a degree of wear in the eraser 402. Information associated with degree of wear in the eraser 402 is received by the control unit 304. The control unit 304 processes this information to determine life expectancy of the eraser 402. In an embodiment, the life expectancy may be represented in the form of rate of life remaining in the eraser 402. The life expectancy information may be periodically monitored and communicated to the control unit 304. The control unit 304 may process the life expectancy information and present it on a display screen 502. In an exemplary embodiment, the life expectancy information may be presented in the form of percentage remaining life of the eraser 402 for example, 50% remaining. Thus, the user can view the life expectation information and understand when the eraser 402 is expected to reach its end of life. The percentage of remaining life may be presented continuously in the display screen 502 so that the user can view the information.

In an embodiment, the control unit 304 may be configured to determine if the rate of life remaining of the eraser 402 falls below a predefined threshold, alarm(s) may be generated by an alarm unit 504. The alarm unit 504 presents this alarm so that user can understand the life of the eraser 402 reduced to a non-acceptable level and hence needs a replacement. The alarm unit 504 may present the alarm in the display screen 502. So when the user uses the medical imaging apparatus then alarm can be easily visible and can be informed to a service engineer to replace the eraser 402. In another embodiment, the alarm unit 504 may be configured to present a sound alarm that can attract the attention of the user in case the user is not operating the medical imaging apparatus. In another exemplary scenario, the alarm may be presented in a mobile device of the user. The mobile device may be communicably connected to the medical imaging apparatus over a wireless communication connection using wireless technology, such as Bluetooth®, wi-fi and so on. Thus, the user can view the alarm in the mobile device and be updated on the status of the eraser 402 when remotely located.

The display screen 502, the alarm unit 504, the life detection unit 500 and the control unit 304 may be embodied in the medical imaging apparatus. The medical imaging apparatus is not shown in FIGS. 3-5 for sake of convenience of illustration, however it may be envisioned that the display screen 502, the alarm unit 504, the life detection unit 500 and the control unit 304 may be configured outside of the medical imaging apparatus but communicably connected.

From the foregoing, it will be appreciated that the above disclosed is a cleaning system for cleaning a slip ring arranged to be rotatable about an axis in a medical imaging apparatus. The cleaning system includes a cleaner assembly that can preprogrammed to automatically clean the slip-ring at periodic time intervals so that the user intervention is reduced. Further, the service engineer need not attend the medical imaging apparatus physically and disassemble the apparatus for cleaning the slip-ring. The life expectancy of the cleaner assembly is continuously monitored and presented to the user so that an informed decision can be made when to replace an eraser in the cleaner assembly. Further an alarm indicating the life expectancy level falling below a required threshold may also help the user earlier to take appropriate steps to replace the eraser.

This written description uses examples to disclose the invention, including the best mode, and also to enable any person skilled in the art to practice the invention, including making and using any computing system or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

I claim:

1. A cleaning system for cleaning a slip ring arranged to be rotatable about an axis, the cleaning system comprises:
   a cleaner assembly configured to be positionable to contact the slip ring, wherein the cleaner assembly is capable of moving along the slip ring for cleaning; and
   a control unit configured to control the functioning of the cleaner assembly based on user input.

2. The cleaning system of claim 1, wherein the cleaner assembly comprises:
   a support unit; and
   an eraser arranged on the support unit, wherein the eraser contacts the slip ring when the support unit moves for cleaning the slip ring.

3. The cleaning system of claim 2, wherein the slip ring is stationary during cleaning.

4. The cleaning system of claim 2 further comprises a dust removing unit configured to remove dust from the cleaner assembly.

5. The cleaning system of claim 4, wherein the dust removing unit comprises:
   a vacuum cup capable of removing the dust from the eraser; and
   a collection unit for collecting the dust removed.

6. The cleaning system of claim 5, wherein the control unit is configured to operate the vacuum cup to remove the dust from the eraser.

7. The cleaning system of claim 2, wherein the control unit is configured to position the cleaner assembly in contact with the slip ring in response to a user's command.

8. The cleaning system of claim 2 further comprises a life detection unit comprising one or more sensors configured to monitor life expectancy of the eraser.

9. The cleaning system of claim 8, wherein the one or more sensors are further configured to measure a degree of wear associated with the eraser.

10. An medical imaging apparatus having a slip ring arranged to be rotatable about an axis, the medical imaging apparatus comprising:
    a cleaner assembly configured to be positionable to contact the slip ring, wherein the cleaner assembly is capable of moving along the slip ring for cleaning; and
    a control unit configured to control the functioning of the cleaner assembly based on user input.

11. The medical imaging apparatus of claim 10, wherein the cleaner assembly comprises:
    a support unit; and
    an eraser arranged on the support unit, wherein the eraser contacts the slip ring when the support unit moves for cleaning the slip ring, wherein the slip ring is stationary while cleaning.

12. The medical imaging apparatus of claim 10, wherein the control unit is configured to position the eraser on the slip ring at predefined interval for cleaning based on the user input.

13. The medical imaging apparatus of claim 10 further comprises a dust removing unit configured to remove dust from the cleaner assembly.

14. The medical imaging apparatus of claim 13, wherein the dust removing unit comprises:
    a vacuum cup capable of removing the dust from the eraser; and
    a collection unit for collecting the dust removed.

15. The medical imaging apparatus of claim 14, wherein the control unit is configured to operate the vacuum cup to remove the dust from the eraser.

16. The medical imaging apparatus of claim 10, wherein the control unit is configured to position the cleaner assembly in contact with the slip ring in response to a user's command.

17. The medical imaging apparatus of claim 10 further comprises a life detection unit comprising one or more sensors configured to monitor life expectancy of the eraser.

18. The medical imaging apparatus of claim 17, wherein:
    the one or more sensors are further configured to measure a degree of wear associated with the eraser; and
    the control unit is configured to present the life expectancy of the eraser to a user.

19. The medical imaging apparatus of claim 17, wherein the control unit is configured to present an alarm indicating expiry of life of the eraser.

20. The medical imaging apparatus of claim 10 further comprises a control panel connected to the control unit, wherein the user operates the control panel to actuate the cleaner assembly for cleaning the slip ring.

* * * * *